US010507197B2

(12) United States Patent
Wu et al.

(10) Patent No.: US 10,507,197 B2
(45) Date of Patent: Dec. 17, 2019

(54) PHARMACEUTICAL COMPOSITION CONTAINING SILIBININ

(71) Applicant: TASLY PHARMACEUTICAL GROUP CO., LTD., Tianjin (CN)

(72) Inventors: Naifeng Wu, Tianjin (CN); Xijun Yan, Tianjin (CN); He Sun, Tianjin (CN); Kaijing Yan, Tianjin (CN); Yonghong Zhu, Tianjin (CN); Shunnan Zhang, Tianjin (CN); Xiaolin Bai, Tianjin (CN); Yi He, Tianjin (CN); Xiaohui Ma, Tianjin (CN); Ting Li, Tianjin (CN); Lei Li, Tianjin (CN)

(73) Assignee: Tasly Pharmaceutical Group Co., Ltd., Tianjin (CN)

( * ) Notice: Subject to any disclaimer, the term of this patent is extended or adjusted under 35 U.S.C. 154(b) by 0 days.

(21) Appl. No.: 15/560,576

(22) PCT Filed: Mar. 22, 2016

(86) PCT No.: PCT/CN2016/077034
§ 371 (c)(1),
(2) Date: Sep. 22, 2017

(87) PCT Pub. No.: WO2016/150375
PCT Pub. Date: Sep. 29, 2016

(65) Prior Publication Data
US 2018/0042892 A1 Feb. 15, 2018

(30) Foreign Application Priority Data
Mar. 23, 2015 (CN) .......................... 2015 1 0128638

(51) Int. Cl.
| *A61K 31/357* | (2006.01) |
| *A61K 36/82* | (2006.01) |
| *A61K 47/24* | (2006.01) |
| *A61K 9/48* | (2006.01) |
| *A61K 31/205* | (2006.01) |
| *A61P 1/16* | (2006.01) |
| *A61K 9/16* | (2006.01) |
| *A61K 31/355* | (2006.01) |
| *A61K 31/683* | (2006.01) |
| *A61K 9/08* | (2006.01) |
| *A61K 36/488* | (2006.01) |

(52) U.S. Cl.
CPC .............. *A61K 31/357* (2013.01); *A61K 9/08* (2013.01); *A61K 9/1617* (2013.01); *A61K 9/1682* (2013.01); *A61K 9/48* (2013.01); *A61K 31/205* (2013.01); *A61K 31/355* (2013.01); *A61K 31/683* (2013.01); *A61K 36/488* (2013.01); *A61K 36/82* (2013.01); *A61K 47/24* (2013.01); *A61P 1/16* (2018.01); *A61K 2236/19* (2013.01)

(58) Field of Classification Search
CPC .. A61K 31/357; A61K 2236/19; A61K 36/82; A61K 47/24; A61K 9/1617; A61K 31/205; A61K 31/355; A61K 31/683; A61K 36/488; A61K 9/08; A61K 9/1682; A61K 9/48; A61K 2300/00; A61K 9/0095; A61K 9/145; A61K 9/2013; A61K 9/4858; A61P 1/16
See application file for complete search history.

(56) References Cited

FOREIGN PATENT DOCUMENTS

| CN | 1961874 A | 5/2007 |
| CN | 102960500 A | 3/2013 |
| CN | 103372169 A | 10/2013 |
| CN | 103830204 A | 6/2014 |
| EP | 0209037 A1 | 1/1987 |
| RU | 2314797 C2 | 1/2008 |
| RU | 2318538 C1 | 3/2008 |

OTHER PUBLICATIONS

International Patent Application No. PCT/CN2016/077034; Int'l Written Opinion and Search Report; dated Jun. 24, 2016; 8 pages.
WPI Database; No. 2013-J59447; Menghai Tea Ind Co. Ltd.; Mar. 2013; 2 pages.
Koo et al.; "Effects of Camellia sinensis Extracts on the Antioxidant System and Alcohol Down-Regulation Enzymes in Sub-Acute Ethanol Treated ICR Mice"; Journal of the Korean Society of Food Science and Nutrition; vol. 36 No. 9; 2007; p. 1134-1139 (abstract only); 4 pages.
Grattagliano et al; "A silybin-phospholipids complex counteracts rat fatty liver degeneration and mitochondrial oxidative changes"; World Journal of Gastroenterology; vol. 19 No. 20; May 2013; p. 3007-3017.
Abascal et al.; "Kudzu—the Miracle Vine"; Alternative & Complementary Therapies; Apr. 2007; p. 78-85.
Matteucci et al.; "Liver Disease in Diabetes Mellitus: Potential Therapeutic Value of Vitamin E-Silybin Phytosomal Complex"; Immunology, Endocrine and Metabolic Agents in Medicinal Chem; vol. 10 No. 2; 2010; p. 84-90.
Liu et al.; "Clinical Effect of Silymarin Combined with Levocarnitine on Nonalcoholic Fatty Liver Disease"; China Modern Medicine; vol. 16 No. 7; Apr. 2009; p. 19-20 (abstract).
Falasca et al.; "Treatment with Silybin-Vitamin E-Phospholipid Complex in Patients with Hepatitis C Infection"; Journal of Medical Virology; vol. 80; 2008; p. 1900-1906.

*Primary Examiner* — Audrea B Coniglio
(74) *Attorney, Agent, or Firm* — BakerHostetler (57) ABSTRACT

Disclosed is a pharmaceutical composition containing silibinin, which is prepared from the following bulk drugs by weight ratio: 8.75-60 parts of silibinin, 15-65 parts of phospholipid, and 25-200 parts of Pu'er tea extract. The drug has the function of treating non-alcoholic fatty liver.

20 Claims, 1 Drawing Sheet

PHARMACEUTICAL COMPOSITION CONTAINING SILIBININ

CROSS-REFERENCE TO RELATED APPLICATIONS

This application is the National Stage of International Application No. PCT/CN2016/077034 filed Mar. 22, 2016, which claims the benefit of Chinese application number 201510128638.8, filed Mar. 23, 2015 the disclosures of which are incorporated herein by reference in their entireties.

TECHNICAL FIELD

The present invention relates to the technical field of medicines, and particularly to a pharmaceutical composition containing silibinin for the treatment of hepatopathy.

BACKGROUND ART

In the late 1960s and 1980s, the pharmaceutists of West Germany with H. wagner as representative extracted the active ingredient from the fruit of the Silybummarianum, which was named as silymarin, a new class of flavonoid having a C-9 substituents, i.e., a flavonoid lignans condensed with a dihydroflavonol and a phenylpropanoid derivative. Silibinin (silybin) is one of the main components of silymarin. Pharmacological and toxicological studies have shown that silibinin has the effects of protecting and stabilizing the hepatocyte membrane, promoting the recovery of hepatocyte and improving the liver function. Silibinin has different levels of protection and treatment effects on various types of hepatic injury caused by hepatic poisons such as carbon tetrachloride, thioacetamide, hydroxycholine, phalloidine, mucronatine, etc. And silibinin can be used for treating acute and chronic hepatitis, early hepatocirrhosis, fatty liver, toxic or drug-induced hepatopathy.

The silibinin is poor in water solubility and common organic solvents, resulting in low bioavailability and thereby affecting the clinical efficacy. To improve the bioavailability thereof, domestic and external pharmacy workers have made substantial amounts of work. The measures to improve the absorption of poorly soluble drug are typically superfine grinding, salinization, and the addition of cosolvent, etc. In recent years, the studies have shown that the dissolution and bioavailability are greatly improved by the methods of formulating into cyclodextrin inclusion compound, solid dispersion, synthetic phospholipid complex and formulating into different dosage forms.

From the perspective of solid preparation, the phospholipid complex is a more specific solid dispersion, which has a fixed melting point, is a molecular compound (complex) whose chemical nature is more stable and different from the compound of drug and phospholipid, such compounds varies with the types of phospholipid and ratios of drug to phospholipid, and a phospholipid molecule can be bound with a different number of drug molecules. Deduced from the spectroscopy characteristics of the complex, the drug has a strong interaction with the polar groups of the phospholipid, which inhibits the free rotation of the single chains in the molecule, whereas the two long fatty acid chains of the phospholipid do not participate in the complex reaction and are free to shift and wrap the polar portions of the phospholipid to form a lipophilic surface, so that the complex shows strong lipid solubility. The complex changes the physiochemical properties of drug, and thus increases the lipid solubility of the drugs and reduces the water solubility of the drugs, and promotes the combination of drug molecules and cell membranes to improve the absorption and increases the bioavailability of the drug.

Pu'er tea is a unique and famous tea in Yunnan province. The locality has moderate climate, abundant rainfall and is mist-shrouded. Pu'er tea is divided into two series by Yunan big leaf species sun-dry tea and reprocessing thereof: the unzymic Pu'er tea by directly re-processing into the finished product and the enzymic Pu'er tea by re-processing after the artificial accelerated fermentation, and the patterns of which are divided into loose tea and compressed tea; natural aging process is also persistently carried out after the finished products, with the unique qualities gets better.

Pu'er tea is the only post-fermented tea, and substances harmful to the human body such as theophylline, tea polyphenols are degraded in the long process of fermentation, so the product is mild, does not stimulate the body, and also can promote metabolism, accelerate the digestion and transformation of fats and toxins in the body. For the problems of obesity and three-hypes which are puzzling urbanites, Pu'er tea can play a good mitigation effect, such as expelling of toxin, nourishing the stomach, anti-inflammatory, reducing the cholesterol, off lipid and removing grease, cosmetic slimming. Modern technologies show that Pu'er tea can improve insulin resistance, regulate levels of blood lipid and leptin, etc., and can block the fat accumulation of hepatic parenchymal cell caused by insulin resistance to some extent.

Non-alcoholic fatty liver disease (NAFLD) is a metabolic stress-induced hepatic injury that is closely related to insulin resistance and genetic susceptibility, the pathological changes of which are similar to alcoholic fatty liver disease. NAFLD is a clinicopathological syndrome characterized by steatosis and fat storage of hepatocytes in the hepatic lobule but without history of alcohol abuse. NAFLD shows different degrees of hepatic lesion, from simple fatty liver without any inflammation to severe inflammatory response of severe fibrosis and even cirrhosis, mainly includes 3 types: simple fatty liver, steatohepatitis, fatty cirrhosis.

Non-Alcoholic Fatty Liver Disease Treatment:
1. Prevention of protopathies or associated risk factors. 2. Basal treatment: developing a reasonable energy intake and diet adjustment, taking moderate aerobic exercises, correcting bad lifestyles and behaviors. 3. Avoiding aggravating hepatic injury: preventing a sharp decline in weight, drug abuse and other factors that may induce exacerbation of hepatopathy. 4. Weight loss: requiring all NAFLD patients who are overweight, and have visceral obesity and rapid weight gain in the short term to change the lifestyles to control weight and reduce waist circumference. Basal treatment for 6 months, weight loss <0.45 kg per month, or body mass index (BMI) >27 $kg/m^2$ combined with blood lipid, blood glucose, blood pressure and other indicators of more than two abnormalities may consider adding sibutramine or orlistat and other obesity drugs, weight loss per week should not exceed 1.2 Kg (children do not exceed 0.5 Kg per week); BMI >40 $kg/m^2$ or BMI >35 $kg/m^2$ combined with sleep apnea syndrome and other obesity-related diseases, may consider the proximal end gastric bypass procedures to lose weight (II-1, II-2, II-3, III). 5. Insulin sensitizer: combined with type 2 diabetes, impaired glucose tolerance, fasting plasma glucose and visceral obesity, may consider the application of metformin and thiazolidinediones in order to improve insulin resistance and control of blood glucose (II-1, II-2, II-3). 6. Hypolipidemic agents: dyslipidemia, with basal treatment and (or) application of weight loss and hypoglycemic pharmaceuticals for more than 3-6 months, is still mixed with hyperlipidemia or hyperlipidemia, combined with more than 2 risk factors, should consider adding the use of fibrates, statins or probucol and other hypolipidemic drugs (II-1, II-2, II-3). 7. Drugs for hepatopathy: NAFLD associated with hepatic dysfunction, metabolic syndrome, 3-6 months after basal treatment remains ineffective, and liver biopsy shows NASH and chronic progression of the course of the disease, the drug auxiliary treatment for hepatopathy can be used with antioxidant, anti-inflammatory, anti-fibrosis, and related drugs (II-1, II-2, II-3, III) such as polyene phosphatidylcholine, vitamin E, silymarin and ursodeoxycholic acid can be rationally chosen according to drug performance, disease activity and stage of the disease, but multi-drugs should not be applied simultaneously. 8. Liver transplantation: mainly for NASH-related end-stage hepatopathy and some cryptogenic J hepatocirrhosis, and the metabolic condition (III) should be screened before liver transplantation. BMI >40 kg/m² is contraindication to liver transplantation (III).

The above treatments have not been used by being mixed together, such as a combination of hypoglycemic and hepatopathy drugs, or a combination of lipid-lowering and hepatopathy drugs. Therefore, the search for a pharmaceutical with a variety of health-promoting functions cannot wait.

SUMMARY OF THE INVENTION

The present invention provides a pharmaceutical composition. There is good curative effect on non-alcoholic fatty liver, combination of the three also has the synergistic effect for the treatment of non-alcoholic fatty liver.

The present invention provides a method for preparing the pharmaceutical composition.

The present invention also provides the use of the pharmaceutical composition.

The present invention is achieved by the following technical solutions:

The pharmaceutical composition of the present invention is prepared from the following bulk drugs by weight ratio:
  8.75-60 parts of silibinin
  15-65 parts of phospholipid
  25-200 parts of Pu'er tea extract;
preferably, the pharmaceutical composition of the present invention is prepared from the following bulk drugs by weight ratio:
  8.75-60 parts of silibinin
  15-65 parts of phospholipid
  25-150 parts of Pu'er tea extract;
preferably, the pharmaceutical composition of the present invention is prepared from the following bulk drugs by weight ratio:
  25-40 parts of silibinin
  30-50 parts of phospholipid
  80-120 parts of Pu'er tea extract;
most preferably, the pharmaceutical composition of the present invention is prepared from the following bulk drugs by weight ratio:
  35 parts of silibinin
  42 parts of phospholipid
  100 parts of Pu'er tea extract.

The phospholipid according to the present invention is a soybean phospholipid or lecithin based on phosphatidylcholine, preferably soybean phospholipid.

Described silibinin and phospholipid are both known from the prior art or commercially available. In order to better exert the efficacy of the present invention, the silibinin of the present invention is preferably prepared by dissolving silymarin in 80% ethanol, filtering and washing the precipitate with 95% ethanol for three times, collecting the precipitate. The precipitate is dissolved in anhydrous ethanol, filtered, and the filtrate is added with a certain amount of water to separate out the precipitate, and the precipitate is collected by filtration, dried under reduced pressure, pulverized and mixed.

The effect of phospholipid in the present invention is promoting the dissolution and absorption of pharmaceuticals. The silibinin is a low-dissolving and low-permeability pharmaceutical, the solubility of which can be improved after it's combined with phospholipid to form a phospholipid complex, thus enhancing the bioavailability of the pharmaceutical.

The Pu'er tea extract is commercially available, preferably a DEEPURE® Pu'er tea essence. The present invention can also be prepared according to the prior art. In order to better exert the efficacy of the present invention, Pu'er tea essence or Pu'er tea extract is preferably prepared according to the method of patents (publication No. CN101961061A, CN101961061B, CN101961425A, CN101961425B, CN101961060A, CN101961059A, CN101961059B).

For example, said Pu'er tea essence is prepared as follows:
Step 1, Pu'er tea leaves are decocted with 6-12 times the volume of water for 2-4 times, 0.5-2 hours each time; extract solution is filtered, and filtrate is concentrated under reduced pressure and the temperature of ≤70° C. to the weight of tea leaves:the volume of concentrate=1:2-1:3;
Step 2, the concentrate is centrifuged with a centrifuge, the centrifugate is concentrated under reduced pressure to density of 1.1-1.25 at 45-65° C., the concentrated cream is spray dried or microwave dried, obtains final product.

Preferably, the steps are present as follows:
Step 1, Pu'er tea leaves are decocted with 6-12 times the volume of vigorously boiling water for 3 times, 0.5-2 hours each time; extract solution is filtered, and filtrate is concentrated under reduced pressure and the temperature of ≤70° C. to the weight of tea leaves:the volume of concentrate=1:2-1:3;
Step 2, the concentrate is centrifuged with a tripod pendulum type batch centrifugal, the tripod pendulum is centrifuged with a tubular-bowl centrifuge, and the centrifugate is concentrated under reduced pressure to density of 1.1-125 at 45-65° C., concentrated cream is dried or microwave dried, obtains final product;
wherein tubular-bowl centrifuge condition is: centrifuge speed: 15000-19000 rpm/min; spray drying conditions are: inlet temperature: 140-190° C., outlet temperature: 75-95° C.

Most preferably, the steps are present as follows:
Pu'er tea leaves are decocted with vigorously boiling water for 3 times, the first time decocted 1.5 h, 10 times the volume of water added; the second time decocted 1.5 h, 8 times the volume of water added; the third time decocted 1 h, 8 times the volume of water added, extract solution is filtered, and filtrate is concentrated under reduced pressure and the temperature of ≤70° C. to the weight of tea leaves: the volume of concentrate=1:2-1:3, the concentrate is centrifuged with a tripod pendulum type batch centrifugal, the tripod pendulum is centrifuged with a tubular-bowl centrifuge, and the centrifugate is concentrated under reduced pressure to density of 1.1-1.25 at 45-65° C., concentrated cream is spray dried or microwave dried, obtains final product.

wherein tubular-bowl centrifuge condition is: centrifuge speed: 15000-19000 rpm/min; spray drying conditions are: inlet temperature: 140-190° C., outlet temperature: 75-95° C.

The above compositions are made by weight ratios, and may be increased or reduced according to corresponding proportion in production processes, such as large-scale production can be in unit of kg or T (ton); small scale preparations can also be in unit of g. The weight can be increased or reduced, but the proportions of the weight ratio of bulk drugs between the components remain unchanged.

The proportions of the above weight ratio are obtained through scientific screening, for special patients, such as patients with severe or mild symptom, obese or thin patients, the proportions of the amount of composition can be accordingly adjusted, increased or decreased no more than 10%, the efficacy is substantially constant.

Any pharmaceutically acceptable dosage forms can be formulated in the formulation of a pharmaceutical preparation, the dosage forms are selected from: tablet, sugar coated tablet, film coated tablet, enteric coated tablet, capsule, hard capsule, soft capsule, oral liquid, oral agent, granule, pill, powder, paste, sublimed preparation, suspension, solution, injection, suppository, ointment, emplastrum, creme, spray, patch. Preferably oral preparations, and optimal preferably tablet, capsule, granule.

Some pharmaceutically acceptable carriers can be added into the pharmaceutical compositions of the present invention as needed, the pharmaceutical preparations can be prepared using galenic pharmacy conventional techniques, such as mixing the pharmaceutically active substances with pharmaceutically acceptable carriers. The pharmaceutically acceptable carriers are selected from: mannitol, sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, the carbonate, acetate, phosphate of monovalence alkali metal or aqueous solution thereof, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose and derivate thereof, alginate, gelatin, polyvinyl pyrrolidone, glycerine, propylene glycol, ethanol, Tween 60-80, Span-80, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid material, kaolin, talc, calcium stearate, magnesium stearate, etc. Preferably, the carrier is one or more of microcrystalline cellulose, lactose, starch, sodium carboxymethylcellulose, low substituted hydroxypropyl cellulose, talc.

When the pharmaceutical composition of the present invention is prepared into medicament, the unit dosage of the medicament may contain 0.1-1,000 mg of the pharmaceutically active substance of the present invention, and the remainders are pharmaceutically acceptable carriers. The pharmaceutically acceptable carriers may be 0.1-99.9% of the total preparation weight by weight. Preferably, the pharmaceutically acceptable carriers may be 40-70% of the total preparation weight by weight.

The usage and dosage of the pharmaceutical compositions or preparations of the present invention are determined according to the conditions of patients while being used.

The cumulative dissolution rate of the pharmaceutical composition preparations according to the present invention, such as tablets, capsules, granules and so on, is not less than 60% while dissolution in vitro for 2 h and the dissolution rate is greater than or equal to 15% while dissolution in vitro for 30 min, in a dissolution condition: slurry method, rotation speed of 100 rpm and temperature of 370, and release medium is: 1,000 ml of hydrochloric acid solution at pH1.2, dosage: 1 capsule/1 tablet/1 bag granules.

The present invention also provides a preparation method of the pharmaceutical composition of the present invention, and the preparation method comprises the following steps:

① taking a prescription amount of the raw materials for later use;

② (preparation of silibinin complex liquid: weighing a prescription amount of silibinin and phospholipid, dissolving them with anhydrous ethanol, then concentrating and recovering ethanol to a certain volume for later use;

③ granulation: weighing a prescription amount of Pu'er tea extract as a base material, taking the silibinin complex liquid prepared in step ② as a feed liquid, and the granules are prepared by a fluidization spray method with a fluidized bed, i.e., the pharmaceutical compositions of the present invention.

The present invention also includes the preparation step ④, taking the pharmaceutical composition of step ③ and pharmaceutically acceptable carriers, and preparing the pharmaceutically acceptable carriers according to the conventional preparation process.

Preferably, the preparation method of pharmaceutical composition of the present invention, comprises the following steps:

① taking a prescription amount of the raw materials for later use;

② preparation of silibinin complex liquid: weighing a prescription amount of silibinin and phospholipid, and dissolving them in the anhydrous ethanol, heating and refluxing to clarify the solution and continuing to heat for a certain time, then the clear solution is concentrated under reduced pressure to a certain volume, to obtain the silibinin complex liquid for later use;

③ granulation: weighing a prescription amount of Pu'er tea extract as a base material, taking the silibinin complex liquid prepared in step ② as a feed liquid, and the granules are prepared by a fluidization spray method with a fluidized bed, drying after the liquid complex is all sprayed in, to obtain the pharmaceutical compositions for later use;

④ preparation: taking the granules of step ③ and the pharmaceutically acceptable carriers to prepare the conventional preparations.

Wherein the heating time described in step ② is 0.5-1.5 hours; the concentrated volume is 5%-20% of the original volume and the temperature of concentration under reduced pressure is 60-80° C.

Wherein the parameters of the fluidized bed in step ③ are: the temperature of the materials is 40-65° C., during the granulation process, the parameters such as fan frequency, inlet air temperature and infusion frequency are adjusted to keep the materials in good fluidization state, after completing the granulation, the granules are dried for 10-60 minutes, and the drying temperature is 55-65° C.

Pu'er tea can improve insulin resistance, regulate the levels of blood lipid and leptin and other effects, can block the fat accumulation of hepatic parenchymal cell caused by insulin resistance to a certain extent, combined with the strong free radical scavenging and anti-oxidative stress ability of silibinin, the two have preferable anti-NAFLD (non-alcohol fatty liver) effect.

Hereinafter, the advantageous effects of the present invention will be described by experimental examples.

Experimental Example 1 Dissolution Experiment In Vitro

The dissolutions of the silibinin-phospholipid-Pu'er tea compositions obtained in embodiments 16-20 are determined under the following conditions: the selection of the dissolution methods is based on the properties of the main component silibinin in the compositions, the silibinin, as a medicament with low solubility and low permeability, is the fourth category in the Biopharmaceutical Classification System (BCS), dissolution and absorption thereof are both the rate-limiting steps, but the absorption of the pharmaceutical depends on the dissolution, the dissolution stage of silibinin is mainly carried out in the stomach, the absorption stage is mainly carried out in the small intestine, determination of in-vitro dissolution of the pharmaceutical contributes to judge the absorption degree in vivo and further evaluate the efficacy. Therefore, the following dissolution method is chosen to evaluate the composition: slurry method, rotation speed of 100 rpm and temperature of 37° C., and release medium is: 1,000 ml of hydrochloric acid solution at pH1.2, dosage: 1 capsule/1 tablet/1 bag granules. The sampling points are: 15, 30, 45, 60, 90, 120 min. The cumulative dissolution is determined. The results are shown in Table 1 below.

tea, by continuing the absorption improvements of the pharmaceutical by increasing the compatibility of the pharmaceutical and the biofilm after the combination of silibinin and phospholipid, from two aspects of improving the dissolution and absorption to improve the bioavailability of the main component silibinin.

Experimental Example 2 Evaluation of Pharmacodynamics In Vivo

1 Experimental Animals 80 mice with SPF grade and 6-week-old male C57 BL/6 J leptin-deficient (ob/ob), 10 mice with SPF grade and 6 weeks old male C57 BL/6 J (ob/m), provided by the Beijing Huafukang Bioscience Co., Inc., raised in Tasly Institute's pharmacological toxicology research center barrier animal room, at the temperature of 20° C.-25° C., relative humidity of 60%, 5 mice in each cage, lighting time of 12 hours, timely and quantitative feed, ob/ob mice are fed with high fat diet (HFD, D12492), C57 BL/6 J mice are fed with normal diet, both are provided by Beijing Huafukang Bioscience Co., Inc., and free drinking water, daily replacement of padding.

2 Tested Substances

Silibinin-phospholipid complex, provided by Tasly Pharmaceutical Co., Ltd., lot number 500902031; (prepared according to step 1 of embodiment 1 of the present invention); Pu'er tea extract, tan powder, provided by Tasly

TABLE 1

Summary of dissolution results of silibinin-phospholipid-Pu'er tea preparation with different prescription processes (n = 6)

| Time (min) | Cumulative dissolution (%) | | | | | | | |
|---|---|---|---|---|---|---|---|---|
| | Embodiment 1 | Embodiment 16 | Embodiment 17 | Embodiment 18 | Embodiment 19 | Embodiment 20 | Embodiment 22 | Embodiment 23 |
| 15 | 21.32 | 16.95 | 15.41 | 10.63 | 5.73 | 5.70 | 9.87 | 8.67 |
| 30 | 62.0 | 57.02 | 56.60 | 52.62 | 26.61 | 40.54 | 50.09 | 54.31 |
| 45 | 78.8 | 76.45 | 73.35 | 64.27 | 50.02 | 64.95 | 67.82 | 66.28 |
| 60 | 83.8 | 81.46 | 78.05 | 82.11 | 69.39 | 76.71 | 81.98 | 82.05 |
| 90 | 84.7 | 81.52 | 81.22 | 82.63 | 81.74 | 81.87 | 83.45 | 83.18 |
| 120 | 85.4 | 81.58 | 82.88 | 83.58 | 82.92 | 82.11 | 83.99 | 84.02 |

The dissolution of the reference preparation (trade name: Shui Lin Jia, product of Tasly Pharmaceutical Co., Ltd.) is determined and compared with the silibinin-phospholipid-Pu'er tea composition prepared in Embodiments 16-20, and the results are shown in FIG. 1.

Figure 1:
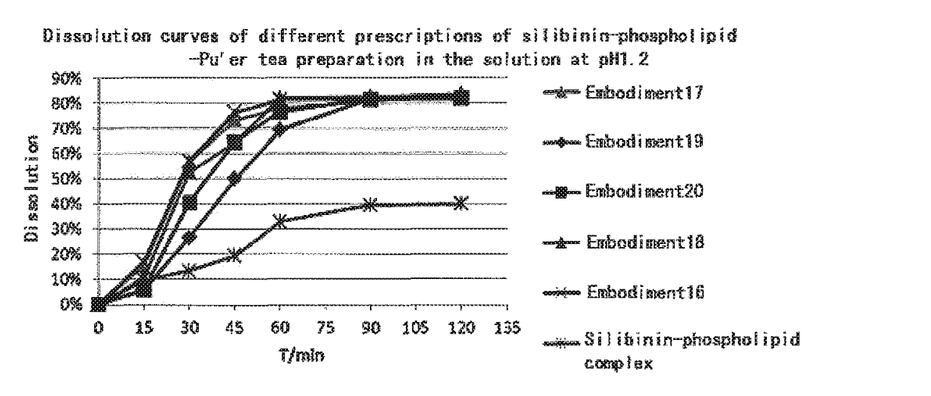
FIG. 1 is an in vitro release curve, wherein, each sample is: reference preparation of Shui Lin Jia, Shui Lin Jia without Pu'er tea, and silibinin-phospholipid-Pu'er tea compositions prepared in embodiments 16-20.

From the data in Table 1 and the curve of FIG. 1 can see:

The in-vitro release of the silibinin-phospholipid-Pu'er tea composition prepared by the preparation method of the present invention is significantly better than that of the reference preparation Shui Lin Jia, which is silibinin-phospholipid complex, surprisingly, the cumulative dissolution of the composition in the hydrochloric acid solution at pH1.2 for 2 h reaches to more than 80%, nearly completely dissolved, increasing to twice of that of the reference formulation, resolving the problems of low solubility and low bioavailability of silibinin that have always existed, which will provide the basis for the studies of dose setting and in-vivo safety and efficacy of silibinin composition in the future.

Pooling the data of in-vitro dissolution experiments and in-vivo pharmacological researches, the present invention further improves the dissolution of the pharmaceutica by combining the silibinin-phospholipid complex with Pu'er Pharmaceutical Co., Ltd., lot number Z001 PE(2014)C06 (H); stored in the sample cabinet of the test room of Pharmacology Institute to be protected from light at room temperature.

3 Experimental Methods 3.1 Experimental Dose Design and Grouping

The experimental animals' administration dose of the silibinin-phospholipid complex is calculated according to the human' daily dose of 3 g (containing silibinin 420 mg, soybean phospholipid 504 mg); the experimental animals' administration dose of the Pu'er tea extract is calculated according to the human' daily dose of 1.2 g; the compatibility proportions and the experimental dose designs of the five different compositions are shown in Table 2, the dose of the experimental animals is set to the clinic equivalent dose of the corresponding tested substances, the formula for calculation is as follows:

animal experimental dose=recommended human dose/60 kg*12.3

TABLE 2

Administration dose of different compositions

|  | Recommended human daily dose (mg) | | | | | Experimental animal dose design (mg/kg) | | | | |
| --- | --- | --- | --- | --- | --- | --- | --- | --- | --- | --- |
| Prescription pharmaceuticals | Embodiment8 | Embodiment9 | Embodiment10 | Embodiment13 | Embodiment14 | Embodiment8 | Embodiment9 | Embodiment10 | Embodiment13 | Embodiment14 |
| Silibinin | 105 | 105 | 210 | 420 | 420 | 21.53 | 21.53 | 86.10 | 86.10 | 86.10 |
| Phospholipid | 195 | 195 | 390 | 504 | 780 | 40.00 | 40.00 | 160.00 | 103.32 | 160.00 |
| Pu'er tea extract | 300 | 1200 | 1200 | 1200 | 1200 | 61.50 | 246.00 | 492.00 | 246.00 | 492.00 |

3.2 Administration of Tested Substances

After 1 week of adaptive feeding, 80 ob/ob mice of 6-week-old are randomly divided into 8 groups: model group, silibinin-phospholipid complex group, Pu'er tea extract group, embodiment 8 group, embodiment 9 group, embodiment 10 group, embodiment 13 group, embodiment 14 group, 10 mice in each group. Another 10 C57BL/6 J mice of 6-week-old are normal group. Normal group mice are fed with normal diet, the model group and the administration group are fed with high fat diet (HFD, D12492). In addition, the mice in different drug intervention groups are given the corresponding doses of drugs by means of intragastric administration, the doses of the five compositions are shown in Table 1, the normal group and model group are given the same amount of distilled water, continuous intragastric administration for 6 weeks.

The mice are free to eat and drink during the experiment, weekly weight, and the doses are adjusted according to the body weight. After the last administration, fasting for 12 h, but water is given, weighing the body weight, extracting rats' eyeballs to collect blood and then put them to death by breaking their necks, and the liver is harvested rapidly, physiological saline rinsing, filter paper blotting and preserved in a −20° C. refrigerator after weighing.

3.3 Detecting Indicators and Methods 3.3.1 General Observation

The weights of mice in each group are measured weekly during the experiment.

3.3.2 Calculation of the Liver Index and Observation of the General Morphology of the Liver After finishing the experiment, the liver is weighed and the liver index is calculated, the liver index (%)=liver wet weight/body weight*100%.

3.3.3 Determination of Serum Biochemical Indexes

Blood of all the mice are collected by extracting rats' eyeballs and centrifuged at 3000 r/min for 15 minutes, the serum is separated and collected in an EP tube and stored at −20° C. refrigerator for later use. The content of glutamic oxaloacetic transaminase (AST), glutamicpyruvic transaminase (ALT), total cholesterol (TC), low-density lipoprotein cholesterol (LDL-C) in serum are measured by 7020 automatic biochemistry instrument.

3.3.4 Insulin Resistant Index

Serum FINS is detected using the Elisa kit and the insulin resistance index is calculated by the formula.

$$Home-IR = \frac{FBG \times FINS}{22.5}$$

3.3.5 Liver Histopathological Examination

Frozen sections are prepared from frozen liver tissue and the degree of hepatic steatosis is observed by oil red O staining. Oil red O staining operation steps: frozen slicing→sufficiently washing with distilled water→staining with oil red O diluent in the dark for 10-15 minutes→taking out 6 ml of oil red O saturated liquid, adding 4 ml of distilled water, leaving it for 5-10 minutes and filtrating for later use→differentiating to interstitial clear under mirror with 60% ethanol→washing with water→nuclear counter staining with hematoxylin→washing with water→sealing piece with neutral gum→microscope observation.

3.4 Data Processing

SPSS 15.0 statistical software is used for analysis, the data are expressed as mean±standard deviation, the t test is used to analyze whether there's any difference between the two groups before and after treatment or not, and the difference is statistically significant with P<0.05.

4 Experimental Results 4.1 The Effects of Each Tested Substance on Body Weight

The weight of mice in each group are measured weekly during the experiment, and the effects of each tested substance on body weight of non-alcoholic fatty liver mice are investigated. As shown in Table 3, the weight of mice in normal group is increased slowly and the weight of mice in model group is increased more rapidly. After 6 weeks of administration, except for the silibinin-phospholipid complex group, the other groups could inhibit the weight increases of mice in different degrees (P<0.01), and there is no significant difference between each groups.

TABLE 3

Effects of each tested substance on body weight of mice (g, n = 10, x̄ ± S)

| Group | Before administration | Administration for 2 weeks | Administration for 4 weeks | Administration for 6 weeks |
| --- | --- | --- | --- | --- |
| Normal | 24.16 ± 1.46 | 26.44 ± 2.01 | 27.07 ± 2.00 | 27.92 ± 1.90 |
| Model | 49.34 ± 2.98 | 55.25 ± 2.68 | 59.26 ± 3.54 | 61.59 ± 4.02 |
| Silibinin-phospholipid complex | 48.46 ± 3.17 | 54.48 ± 4.53 | 58.64 ± 5.41 | 61.12 ± 4.87 |
| Embodiment 8 | 47.97 ± 1.97 | 52.05 ± 2.45** | 54.89 ± 2.93** | 56.84 ± 3.85* |
| Embodiment 9 | 47.83 ± 2.67 | 50.27 ± 2.36** | 52.12 ± 2.12** | 55.57 ± 3.17** |

TABLE 3-continued

Effects of each tested substance on body weight of mice (g, n = 10, x̄ ± S)

| Group | Before administration | Administration for 2 weeks | Administration for 4 weeks | Administration for 6 weeks |
|---|---|---|---|---|
| Embodiment 10 | 47.99 ± 2.81 | 50.86 ± 4.10** | 54.35 ± 3.73** | 56.94 ± 2.57** |
| Embodiment 13 | 48.17 ± 2.78 | 52.31 ± 2.03** | 54.99 ± 2.98** | 57.11 ± 3.92* |
| Embodiment 14 | 48.25 ± 2.16 | 50.89 ± 2.18** | 52.52 ± 1.73** | 56.07 ± 3.55** |

*compared with the model group P < 0.05;
**compared with the model group P < 0.01;

4.2 the Effects of Each Tested Substance on Liver Index

As shown in Table 4, the body weight, liver wet weight and liver index of mice in the model group are significantly increased ($P<0.01$) compared with those in the normal group, and each tested substance can significantly reduce the wet weight and liver index of the mice ($P<0.01$).

TABLE 4

Effects of each tested substance on mice liver index of mice

| Group | Body weight (g) | Liver wet weight (g) | Liver index % |
|---|---|---|---|
| Normal | 25.50 ± 2.50 | 1.03 ± 0.14 | 4.04 ± 0.22 |
| Model | 59.35 ± 2.71 | 4.09 ± 0.45 | 7.10 ± 0.63 |
| Silibinin-phospholipid complex | 58.74 ± 2.94 | 3.67 ± 0.22** | 6.47 ± 0.54** |
| Embodiment 8 | 52.07 ± 1.77** | 2.63 ± 0.22** | 5.05 ± 0.36** |
| Embodiment 9 | 54.13 ± 2.89** | 2.72 ± 0.28** | 5.12 ± 0.55** |
| Embodiment 10 | 51.72 ± 2.69** | 2.90 ± 0.30** | 5.60 ± 0.35** |
| Embodiment 13 | 53.07 ± 1.77** | 2.64 ± 0.25** | 5.05 ± 0.56** |
| Embodiment 14 | 52.97 ± 3.25** | 2.44 ± 0.75** | 4.69 ± 0.38** |

*compared with the model group P < 0.05;
**compared with the model group P < 0.01;

4.3 Effects of Each Tested Substance on Blood Lipid, Liver Function and Insulin Resistance Index As shown in Table 5, the levels of serum TC, LDL, ALT, AST and insulin resistance index are significantly increased in non-alcoholic fatty liver model mice compared with the normal group ($P<0.05$). The silibinin-phospholipid complex shows no significant improvement in the abnormally elevated index ($P>0.05$). The compositions of each embodiments can improve the abnormal elevation of blood lipid, liver function and insulin resistance index in different degrees, and the effect is better than the two used alone; wherein, in embodiments 18-20, serum TC, LDL, ALT, AST and insulin resistance index are reduced significantly ($P<0.05$); in embodiment 16, serum TC and insulin resistance index can be reduced ($P<0.05$), but serum LDL, ALT and AST are not improved significantly ($P>0.05$); in embodiment 17, serum TC, ALT and insulin resistance index can be reduced ($P<0.05$), but LDL and AST are not improved significantly ($P>0.05$).

TABLE 5

Effects of each tested substance on blood lipid, liver function and insulin resistance index of mice

| Group | TC | LDL-C | ALT | AST | Insulin resistant index |
|---|---|---|---|---|---|
| Normal | 3.38 ± 0.19 | 0.27 ± 0.05 | 58.89 ± 35.26 | 94.80 ± 24.05 | 0.60 ± 0.13 |
| Model | 10.07 ± 0.21 | 2.11 ± 0.56 | 448.26 ± 70.83 | 180.98 ± 38.56 | 1.17 ± 0.23 |
| Silibinin-phospholipid complex | 9.68 ± 1.10 | 1.90 ± 0.52 | 404.67 ± 102.01 | 140.28 ± 51.44 | 1.09 ± 0.41 |
| Embodiment 10 | 7.95 ± 0.78** | 1.58 ± 0.19* | 256.48 ± 113.02** | 124.78 ± 53.41** | 0.84 ± 0.24** |
| Embodiment 13 | 8.48 ± 0.58** | 1.42 ± 0.41** | 249.51 ± 133.14** | 125.32 ± 37.71** | 0.80 ± 0.24** |
| Embodiment 14 | 6.48 ± 0.54** | 1.20 ± 0.19** | 185.53 ± 57.00** | 114.01 ± 30.06* | 0.75 ± 0.15** |

*compared with the model group P < 0.05;
**compared with the model group P < 0.01;

4.4 Effects of Each Tested Substance on Liver Pathology in Mice

Oil red O staining: according to the size and number of red particles in hepatocytes of liver frozen issues stained by Oil red O under light microscope, it is divided into mild, moderate and severe type. Mild, that is, ⅓-⅔ of red granules are shown per unit area under light microscope, graded as 1 point; moderate, that is, more than ⅔ of the hepatocytes containing red particles, graded as 2 points; severe, that is, almost all of the hepatocytes containing red particles, graded as 3 points; no steatosis is observed, graded as 0 points.

As shown in Table 6, steatosis occurs in nearly all the hepatocytes in the liver tissues of the model group, and the pathological scores are significantly increased than that in the normal group ($P<0.01$); there is no significant improvement on liver pathological scores by using silibinin-phospholipid complex or Pu'er tea extract alone ($P>0.05$); the combination of the two can improve liver steatosis in different degrees, and the effect is better than that of the two used alone; wherein, the embodiments 16, 18, 19 and 20 can significantly reduce the pathological scores ($P<0.05$); combination 17 has a tendency to reduce the pathological scores ($P>0.05$).

TABLE 6

Effects of each tested substance on liver pathology of mice

| Group | Oil red O staining pathological score |
|---|---|
| Normal | 0.000 ± 0.000 |
| Model | 2.900 ± 0.316 |
| Silibinin-phospholipid complex | 2.800 ± 0.422 |

TABLE 6-continued

Effects of each tested substance on liver pathology of mice

| Group | Oil red O staining pathological score |
|---|---|
| Pu'er tea extract | 2.600 ± 0.516 |
| Embodiment 8 | 2.333 ± 0.707* |
| Embodiment 10 | 2.300 ± 0.675* |
| Embodiment 13 | 2.400 ± 0.516* |
| Embodiment 14 | 1.800 ± 0.632** |

*compared with the model group P < 0.05;
**compared with the model group P < 0.01;

5 Experimental Conclusions

The above experimental results show that: the body weight, liver index, blood lipid, ALT, AST and insulin resistance index are significantly increased in the mice of the non-alcoholic fatty liver model group compared with those in the blank group, and the liver tissues are severe steatosis. Pu'er tea can improve insulin resistance, regulate blood lipids, combined with the strong free radical scavenging and anti-oxidative stress ability of silibinin, the combination use of the two has improved liver steatosis significantly, and the effect is better than that of the two used alone, and having synergistic effect.

DETAILED DESCRIPTION OF THE INVENTION

Hereinafter, detailed description of the present invention will be described in further detail with reference to embodiments and experimental examples so as to more clearly describe the advantages and features of the present invention. But these embodiments are only exemplary and are not intended to limit the scope of the present invention. It will be understood by those skilled in the art that various modifications and substitutions may be made to the details and forms of the present invention without departing from the spirit and scope of the present invention, but that such modifications and substitutions fall within the scope of the present invention. The present invention is further illustrated by the following specific embodiments, but is not intended to be limiting of the present invention.

Embodiment 1

Taking 26.25 g of silibinin, 45 g of soybean phospholipid, 75 g of Pu'er tea extract.
①  Preparation of silibinin complex liquid: weighing a prescription amount of silibinin, soybean phospholipid, and dissolving them in the anhydrous ethanol, heating and refluxing to clarify the solution and continuing to heat for 1 h, then concentrated under reduced pressure and recycling the ethanol to 15% of the original volume for later use;
②  Granulation: weighing a prescription amount of Pu'er tea extract as a base material, taking the silibinin complex liquid prepared in step ① as a feed liquid, preparing granules by a fluidization spray method with a fluidized bed, controlling the temperature of materials at 40° C., drying at 60° C. for 20 min after the liquid complexes are all sprayed in, bagging, made into 1,000 bags of granules.

Embodiment 2

Taking 180 g of silibinin, 195 g of soybean phospholipid, 450 g of Pu'er tea extract.
①  Preparation of silibinin complex liquid: weighing a prescription amount of silibinin, soybean phospholipid, and dissolving them in the anhydrous ethanol, heating and refluxing to clarify the solution and continuing to heat for 1.5 h, then concentrated under reduced pressure and recycling the ethanol to 20% of the original volume for later use;
②  Granulation: weighing a prescription amount of Pu'er tea extract as a base material, taking the silibinin complex liquid prepared in step ① as a feed liquid, preparing the granules by a fluidization spray method with a fluidized bed, controlling the temperature of materials at 65° C., drying at 65° C. for 60 min after the liquid complexes are all sprayed in, bagging, made into 1,000 bags of granules.

Embodiment 3

Taking 26.25 g of silibinin, 195 g of soybean phospholipid, 450 g of Pu'er tea extract.
①  Preparation of silibinin complex liquid: weighing a prescription amount of silibinin, soybean phospholipid, and dissolving them in the anhydrous ethanol, heating and refluxing to clarify the solution and continuing to heat for 0.5 hours, then concentrated under reduced pressure and recycling the ethanol to 5% of the original volume for later use;
②  Granulation: weighing a prescription amount of Pu'er tea extract as a base material, taking the silibinin complex liquid prepared in step ① as a feed liquid, preparing the granules by a fluidization spray method with a fluidized bed, controlling the temperature of materials at 50° C., drying at 55° C. for 10 min after the liquid complexes are all sprayed in, bagging, made into 1,000 bags of granules.

Embodiment 4

Taking 26.25 g of silibinin, 195 g of soybean phospholipid, 75 g of Pu'er tea extract, and preparing 1,000 bags of granules according to the method of embodiment 1.

Embodiment 5

Taking 180 g of silibinin, 45 g of soybean phospholipid, 75 g of Pu'er tea extract, and preparing 1,000 bags of granules according to the method of embodiment 1.

Embodiment 6

Taking 180 g of silibinin, 45 g of soybean phospholipid, 450 g of Pu'er tea extract, and preparing 1,000 bags of granules according to the method of embodiment 1.

Embodiment 7

Taking 180 g of silibinin, 195 g of soybean phospholipid, 75 g of Pu'er tea extract, and preparing 1,000 bags of granules according to the method of embodiment 1.

Embodiment 8

Taking 26.25 g of silibinin, 48.75 g of soybean phospholipid, 75 g of Pu'er tea extract, and preparing 1,000 bags of granules according to the method of embodiment 1.

Embodiment 9

Taking 26.25 g of silibinin, 48.75 g of soybean phospholipid, 300 g of Pu'er tea extract, and preparing 1,000 bags of granules according to the method of embodiment 1.

Embodiment 10

Taking 52.5 g of silibinin, 97.5 g of soybean phospholipid, 300 g of Pu'er tea extract, and preparing 1,000 bags of granules according to the method of embodiment 1.

Embodiment 11

Taking 75 g of silibinin, 90 g of soybean phospholipid, 240 g of Pu'er tea extract, and preparing 1,000 bags of granules according to the method of embodiment 1.

Embodiment 12

Taking 90 g of silibinin, 108 g of soybean phospholipid, 270 g of Pu'er tea extract, and preparing 1,000 bags of granules according to the method of embodiment 1.

Embodiment 13

Taking 105 g of silibinin, 126 g of soybean phospholipid, 300 g of Pu'er tea extract, and preparing 1,000 bags of granules according to the method of embodiment 1.

Embodiment 14

Taking 105 g of silibinin, 195 g of soybean phospholipid, 300 g of Pu'er tea extract, and preparing 1,000 bags of granules according to the method of embodiment 1.

Embodiment 15

Taking 120 g of silibinin, 150 g of soybean phospholipid, 360 g of Pu'er tea extract, and preparing 1,000 bags of granules according to the method of embodiment 1.

Embodiment 16

Taking the granules of embodiment 8, adding 494 g of microcrystalline cellulose and 56 g of sodium carboxymethyl starch, mixing uniformly, encapsulated into No. 0 capsules to obtain 1,000 capsules.

Embodiment 17

Taking the granules of embodiment 9, adding 269 g of microcrystalline cellulose and 56 g of sodium carboxymethyl starch, mixing uniformly, encapsulated into No. 0 capsules to obtain 1,000 capsules.

Embodiment 18

Taking the granules of embodiment 10, adding 194 g of microcrystalline cellulose and 56 g of sodium carboxymethyl starch, mixing uniformly, encapsulated into No. 0 capsules to obtain 1,000 capsules.

Embodiment 19

Taking the granules of embodiment 13, adding 169 g of microcrystalline cellulose, mixing uniformly, encapsulated into No. 0 capsules to obtain 1,000 capsules.

Embodiment 20

Taking the granules of embodiment 14, adding 44 g of microcrystalline cellulose and 56 g of sodium carboxymethyl starch, mixing uniformly, encapsulated into No. 0 capsules to obtain 1,000 capsules.

Embodiment 21

Taking the granules of embodiment 8, adding 400 g of lactase, 94 g of starch and 56 g of sodium carboxymethyl starch, mixing uniformly, encapsulated into No. 0 capsules to obtain 1,000 capsules.

Embodiment 22

Taking the granules of embodiment 13, adding 80 g of lactase, 10 g of talc and 79 g of low-substituted hydroxypropyl cellulose, mixing uniformly, encapsulated into No. 0 capsules to obtain 1,000 capsules.

Embodiment 23

Taking the granules of embodiment 13, adding into 169 g of microcrystalline cellulose, mixing uniformly, tablet pressing to obtain 1,000 tablets.

The invention claimed is:

1. A pharmaceutical composition comprising a mixture of three bulk drugs, wherein the mixture consists of
   8.75-60 parts by weight of silibinin;
   15-65 parts by weight of phospholipid; and
   25-200 parts by weight of Pu'er tea extract,
   wherein parts by weight is the weight ratio of each bulk drug in the mixture.

2. A pharmaceutical composition according to claim 1 comprising
   25-40 parts by weight of silibinin;
   30-50 parts by weight of phospholipid; and
   80-120 parts by weight of Pu'er tea extract.

3. A pharmaceutical composition according to claim 1 comprising
   35 parts by weight of silibinin;
   42 parts by weight of phospholipid; and
   100 parts by weight of Pu'er tea extract.

4. A pharmaceutical preparation comprising the pharmaceutical composition according to claim 1, further comprising pharmaceutically acceptable carriers;
   wherein the pharmaceutical preparation consists of the mixture of the three bulk drugs and the pharmaceutically acceptable carriers, and wherein the pharmaceutically acceptable carriers are 0.1-99.9% by weight of the pharmaceutical preparation.

5. The pharmaceutical preparation according to claim 4, wherein the pharmaceutically acceptable carriers are selected from the group consisting of mannitol, sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose or a derivate thereof, alginate, gelatin, polyvinyl pyrrolidone, glycerine, propylene glycol, ethanol, polysorbate 60-80, sorbitan monooleate, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid, kaolin, talc, calcium stearate, magnesium stearate, microcrystalline cellulose, and a carbonate, acetate, or phosphate salt of a monovalent alkali metal.

6. The pharmaceutical preparation according to claim 4, wherein the pharmaceutical preparation is selected from the group consisting of a tablet, sugar coated tablet, film coated tablet, enteric coated tablet, capsule, hard capsule, soft capsule, oral liquid, oral agent, granule, pill, powder, paste, sublimed preparation, suspensoid, solution, injection, suppository, ointment, emplastrum, creme, spray, and patch.

7. A method of preparing the pharmaceutical preparation according to claim 4, comprising:
  (1) taking a prescription amount of raw materials for later use;
  (2) preparing a silybin complex liquid by weighing a prescription amount of silybin and a phospholipid, and dissolving them in anhydrous ethanol, heating and refluxing to clarify the solution and continuing to heat for a time, then concentrating the clear solution under reduced pressure to a concentrated volume, to obtain the silybin complex liquid;
  (3) granulating by weighing a prescription amount of Pu'er tea extract as a base material, taking the silibinin complex liquid prepared in step (2) as a feed liquid, preparing granules by a fluidization spray method with a fluidized bed, and then drying to obtain the granules;
  (4) combining the granules of step (3) and the pharmaceutically acceptable carriers to obtain the pharmaceutical preparation.

8. The method according to claim 7, wherein step (2), the heating time is 0.5-1.5 hours; and concentrating at 60-80° C. to the concentrated volume that is 5%-20% of the original volume.

9. The method according to claim 7, wherein step (3), during the granulation process the temperature of the fluidized bed is 40-65° C., and adjusting fan frequency, inlet air temperature and infusion frequency to keep the granules fluidized; and wherein the granules are dried for 10-60 minutes at 55-65° C.

10. A method of using the pharmaceutical composition of claim 1 for treating non-alcoholic fatty liver, comprising administering a therapeutically effective amount of the pharmaceutical preparation to a subject in need thereof.

11. A pharmaceutical preparation comprising the pharmaceutical composition according to claim 2, further comprising pharmaceutically acceptable carriers;
  wherein the pharmaceutical preparation consists of the mixture of three bulk drugs and the pharmaceutically acceptable carriers, and wherein the pharmaceutically acceptable carriers are 0.1-99.9% by weight of the pharmaceutical preparation.

12. The pharmaceutical preparation according to claim 11, wherein the pharmaceutically acceptable carriers are selected from the group consisting of mannitol, sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose or a derivate thereof, alginate, gelatin, polyvinyl pyrrolidone, glycerine, propylene glycol, ethanol, polysorbate 60-80, sorbitan monooleate, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid, kaolin, talc, calcium stearate, magnesium stearate, microcrystalline cellulose, and a carbonate, acetate, or phosphate salt of a monovalent alkali metal.

13. The pharmaceutical preparation according to claim 11, wherein the pharmaceutical preparation is of a tablet, sugar coated tablet, film coated tablet, enteric coated tablet, capsule, hard capsule, soft capsule, oral liquid, oral agent, granule, pill, powder, paste, sublimed preparation, suspensoid, solution, injection, suppository, ointment, emplastrum, creme, spray, and patch.

14. A pharmaceutical preparation comprising the pharmaceutical composition according to claim 3, further comprising pharmaceutically acceptable carriers;
  wherein the pharmaceutical preparation consists of the mixture of three bulk drugs and the pharmaceutically acceptable carriers, and wherein the pharmaceutically acceptable carriers are 0.1-99.9% by weight of the pharmaceutical preparation.

15. The pharmaceutical preparation according to claim 14, wherein the pharmaceutically acceptable carriers are selected from the group consisting of mannitol, sorbitol, sorbic acid or sylvite, sodium metabisulfite, sodium bisulfite, sodium thiosulfate, cysteine hydrochloride, mercaptoacetic acid, methionine, vitamin A, vitamin C, vitamin E, vitamin D, azone, disodium EDTA, calcium disodium EDTA, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, lactose, mannitol, silicon derivative, cellulose and derivate thereof, alginate, gelatin, polyvinyl pyrrolidone, glycerine, propylene glycol, ethanol, polysorbate 60-80, sorbitan monooleate, beeswax, lanolin, liquid paraffin, cetyl alcohol, gallic acid esters, agar, triethanolamine, basic amino acid, urea, allantoin, calcium carbonate, calcium bicarbonate, surfactant, polyethylene glycol, cyclodextrin, beta-cyclodextrin, phospholipid material, kaolin, talc, calcium stearate, magnesium stearate, microcrystalline cellulose, and a carbonate, acetate, or phosphate salt of a monovalent alkali metal.

16. The pharmaceutical preparation according to claim 14, wherein the pharmaceutical preparation is selected from the group consisting of a tablet, sugar coated tablet, film coated tablet, enteric coated tablet, capsule, hard capsule, soft capsule, oral liquid, oral agent, granule, pill, powder, paste, sublimed preparation, suspensoid, solution, injection, suppository, ointment, emplastrum, creme, spray, or patch.

17. A method of preparing the pharmaceutical preparation according to claim 14, comprising:
  (1) taking a prescription amount of raw materials for later use;
  (2) preparing a silybin complex liquid by weighing a prescription amount of silybin and a phospholipid, and dissolving them in anhydrous ethanol, heating and refluxing to clarify the solution and continuing to heat for a time, then concentrating the clear solution under reduced pressure to a concentrated volume, to obtain the silybin complex liquid;

(3) granulating by weighing a prescription amount of Pu'er tea extract as a base material, taking the silibinin complex liquid prepared in step (2) as a feed liquid, preparing granules by a fluidization spray method with a fluidized bed, and then drying to obtain the granules;

(4) combining the granules of step (3) and the pharmaceutically acceptable carriers to obtain the pharmaceutical preparation.

18. The method according to claim 17, wherein step (2), the heating time is 0.5-1.5 hours; and concentrating at 60-80° C. to the concentrated volume that is 5%-20% of the original.

19. The method according to claim 17, wherein step (3), during the granulation process the temperature of the fluidized bed is 40-65° C., and adjusting fan frequency, inlet air temperature and infusion frequency to keep the granules fluidized; and wherein the granules are dried for 10-60 minutes at 55-65° C.

20. A method of using the pharmaceutical preparation of claim 4 for treating non-alcoholic fatty liver, comprising administering a therapeutically effective amount of the pharmaceutical preparation to a subject in need thereof.

* * * * *